United States Patent
Hollopeter et al.

(10) Patent No.: US 10,271,398 B2
(45) Date of Patent: Apr. 23, 2019

(54) ADAPTIVE SHADOW CONTROL SYSTEM FOR A SURGICAL LIGHTING SYSTEM

(71) Applicant: American Sterilizer Company, Mentor, OH (US)

(72) Inventors: Michael Hollopeter, Kirtland, OH (US); David Jesurun, South Euclid, OH (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 15/642,379

(22) Filed: Jul. 6, 2017

(65) Prior Publication Data

US 2018/0124892 A1 May 3, 2018

Related U.S. Application Data

(60) Provisional application No. 62/415,595, filed on Nov. 1, 2016.

(51) Int. Cl.
*H05B 33/08* (2006.01)
*A61B 90/30* (2016.01)

(52) U.S. Cl.
CPC ......... *H05B 33/0854* (2013.01); *A61B 90/30* (2016.02); *H05B 33/0842* (2013.01); *A61B 2090/309* (2016.02)

(58) Field of Classification Search
CPC ............... H05B 33/0803; H05B 37/02; H05B 37/0227; A61B 90/30; F21W 2131/205; F21W 2131/202
See application file for complete search history.

(56) References Cited

U.S. PATENT DOCUMENTS

| | | | |
|---|---|---|---|
| 5,526,245 A | 6/1996 | Davis et al. | 362/233 |
| 6,513,962 B1 | 2/2003 | Mayshack et al. | 362/583 |
| 6,601,985 B1 | 8/2003 | Jesurun et al. | 362/572 |
| 6,655,817 B2 | 12/2003 | Devlin et al. | 362/233 |
| 6,880,957 B2 | 4/2005 | Walters | 362/276 |
| 7,311,410 B2 | 12/2007 | Marka | 362/33 |
| 7,513,645 B2 | 4/2009 | Marka et al. | 362/250 |
| 7,746,009 B2 | 6/2010 | Held et al. | 315/362 |
| 7,841,731 B2 | 11/2010 | Marka et al. | 362/85 |
| 8,050,547 B2 | 11/2011 | Fornasiero | 396/4 |
| 8,300,906 B2 * | 10/2012 | Voelker | F21V 21/403 348/370 |
| 8,817,085 B2 | 8/2014 | Hiltl et al. | 348/61 |

(Continued)

FOREIGN PATENT DOCUMENTS

| | | | | |
|---|---|---|---|---|
| CN | 203628472 U | 6/2014 | | F21S 8/06 |
| EP | 1568937 A1 | 8/2005 | | F21S 8/00 |

*Primary Examiner* — Tung X Le
*Assistant Examiner* — Borna Alaeddini
(74) *Attorney, Agent, or Firm* — Kusner & Jaffe (57) ABSTRACT

An adaptive shadow control system that compensates for blockage of one lighthead of a surgical lighting system by increasing the light output from one or more other lightheads of the lighting system. The system also includes control logic for automatic enablement/disablement of adaptive shadow control by detecting whether there is blockage of a lighthead and whether the respective light beams of a plurality of lightheads are being aggregated to form a single aggregated co-illumination light pattern at a work area.

14 Claims, 9 Drawing Sheets

(56) References Cited

U.S. PATENT DOCUMENTS

| | | | |
|---|---|---|---|
| 9,016,916 B2* | 4/2015 | Marka | A61B 90/35 362/572 |
| 9,035,555 B2 | 5/2015 | Fornasiero et al. | 315/129 |
| 9,057,492 B2 | 6/2015 | Van Herpen et al. | 362/147 |
| 9,491,835 B2* | 11/2016 | Elfring | F21V 23/0471 |
| 2003/0185009 A1 | 10/2003 | Walters | 362/276 |
| 2004/0129860 A1 | 7/2004 | Thibaud et al. | 250/205 |
| 2004/0155844 A1 | 8/2004 | Stopa | 245/82 |
| 2005/0083697 A1 | 4/2005 | Filep | 362/285 |
| 2007/0014567 A1 | 1/2007 | Rossner et al. | 396/429 |
| 2008/0192483 A1 | 8/2008 | Mangiardi | 362/319 |
| 2008/0287924 A1 | 11/2008 | Mangiardi | 606/1 |
| 2014/0268855 A1 | 9/2014 | Gerardo | 36/520 |
| 2015/0035437 A1 | 2/2015 | Panopoulos et al. | 315/112 |
| 2015/0180585 A1 | 6/2015 | Sattler | H04B 10/60 |
| 2015/0208478 A1* | 7/2015 | Sattler | H05B 37/02 315/151 |
| 2016/0174336 A1 | 6/2016 | Elfring et al. | H05B 37/0227 |
| 2017/0030573 A1 | 2/2017 | Alexanderson et al. | F21V 33/0068 |

\* cited by examiner

ADAPTIVE SHADOW CONTROL SYSTEM FOR A SURGICAL LIGHTING SYSTEM

RELATED APPLICATIONS

This application claims the benefit of U.S. Provisional Application No. 62/415,595, filed Nov. 1, 2016, said provisional application is hereby fully incorporated herein by reference.

FIELD OF THE INVENTION

The present invention relates generally to surgical lighting systems, and more particularly to an adaptive shadow control and co-illumination control for a surgical lighting system.

BACKGROUND OF THE INVENTION

The present invention relates to the field of surgical lighting systems and problems associated therewith. In one aspect, shadow control is an important element of lighting system performance because it minimizes the contrast of shadow edges cast and minimizes reductions in illumination due to lighthead blockage, thereby providing a uniform lighting field having consistent light intensity. A typical surgical lighting system includes at least one surgical lighthead (also referred to as a "luminaire"), wherein each lighthead is formed of a plurality of lighting modules. Typically, each lighting module is comprised of a plurality of LEDs (i.e., light emitting diodes).

Shadow control minimizes shadows (e.g., by diluting shadows) and/or minimizes the loss of illumination at a work area that results from a blockage between a lighthead and the work area (e.g., a surgical site). Such blockage is commonly caused by the presence of a person's head (e.g., a surgeon or surgical assistant) located between the lighthead and the work area. Shadow control may be implemented using a passive or an adaptive (i.e., active/automatic) shadow control system.

Passive shadow control has been accomplished by increasing the effective area of the source lighting, such as by use of a large reflector, or by use of a plurality of separately-controlled lighting partitions spaced over a large area (i.e., multiple light sources).

Adaptive shadow control detects whether a lighthead has been blocked by (i) directly sensing blockage of the lighthead via proximity sensors or imaging techniques, or (ii) indirectly sensing blockage, through a sensed loss of luminance (i.e., sensing reduced reflected light from the work area). In the direct sensing approach, the light output of the lighthead's blocked light partitions is decreased (thereby reducing wasted light and minimizing irradiance on the surgeon's head), while the light output of the lighthead's unblocked light modules is increased to compensate for the loss of illumination due to the blockage. In the indirect sensing approach, the light output of the lighthead is adjusted to maintain a desired luminance, regardless of whether changes to the lighting conditions are due to a blockage or a change in the surgical albedo (i.e., the proportion of incident light that is reflected by a surface at the work area).

In prior art surgical lighting systems, shadow control is limited to adjusting the light intensity of the lighting partitions in a single lighthead due to a blockage incurred with respect to that same lighthead. Accordingly, excess lighting capability is limited to the lighting partitions of the unblocked regions of a single lighthead.

Figure 1A:
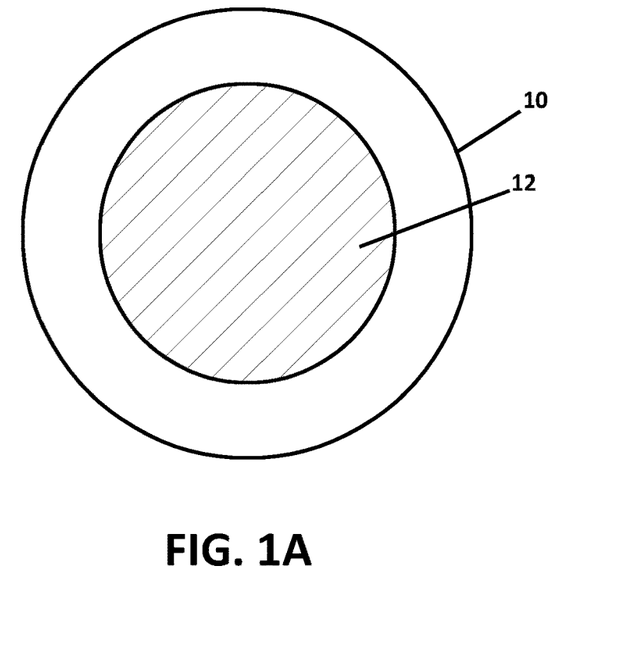
FIG. 1A shows a single mask projected onto a lighthead.
Figure 1B:
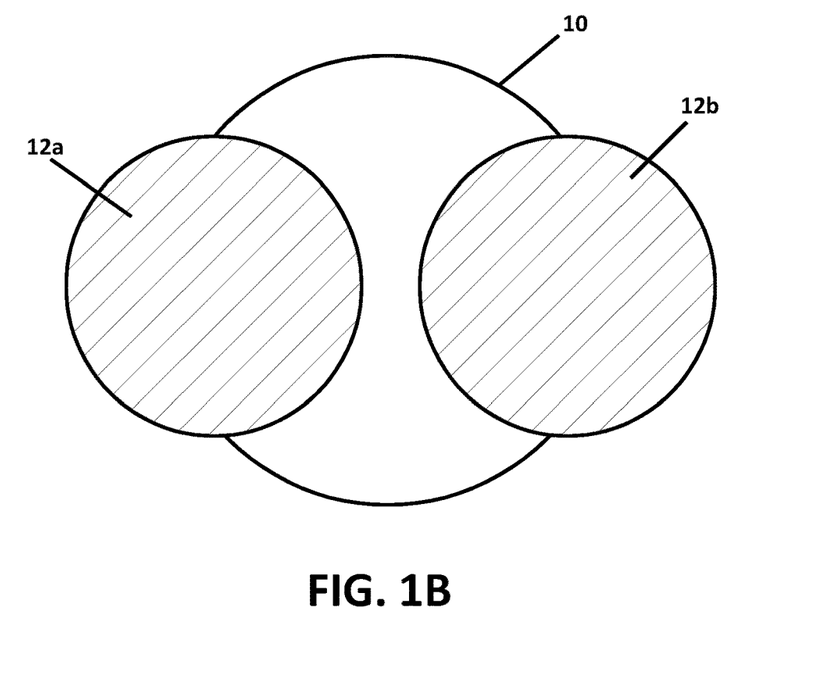
FIG. 1B shows dual masks projected onto a lighthead.

Reference is now made to INTERNATIONAL STANDARD IEC 60601-2-41 of the International Electrotechnical Commission (Medical electrical equipment—Part 2-41: Particular requirements for the safety of surgical luminaires and luminaires for diagnosis). This international standard requires testing for illuminance that remains after a light beam from a lighthead 10 is obstructed by one mask 12 (FIG. 1A) or two masks 12a, 12b (FIG. 1B) that emulate a surgeon's head located between the lighthead 10 and the work area. Since nearly 50% of the light emitting area is blocked in the one mask and two mask scenarios, compensation for lost illuminance requires 100% "excess" lumen output (i.e., double light output capacity).

Figure 2A:
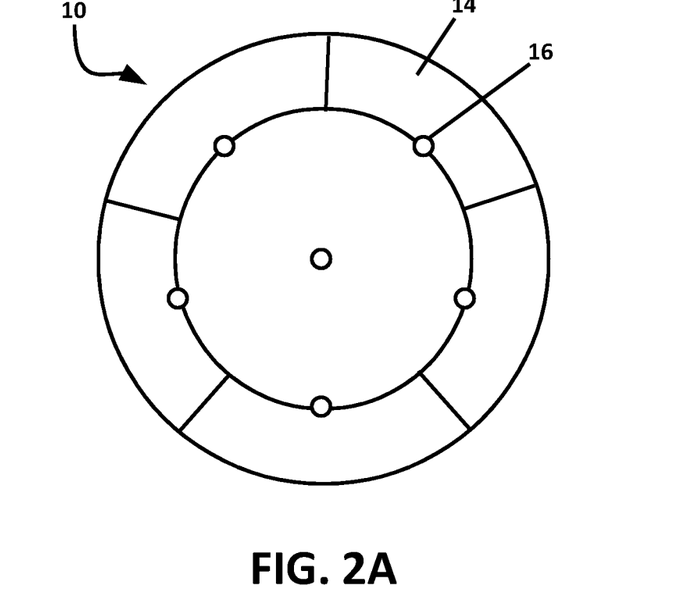
FIG. 2A shows a lighthead having five (5) lighting partitions.
Figure 2B:
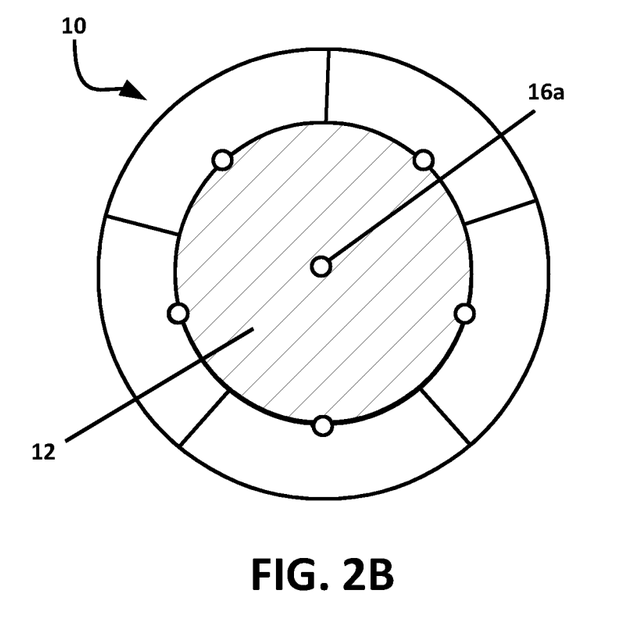
FIG. 2B shows a single mask projected onto a lighthead having five (5) lighting partitions.
Figure 2C:
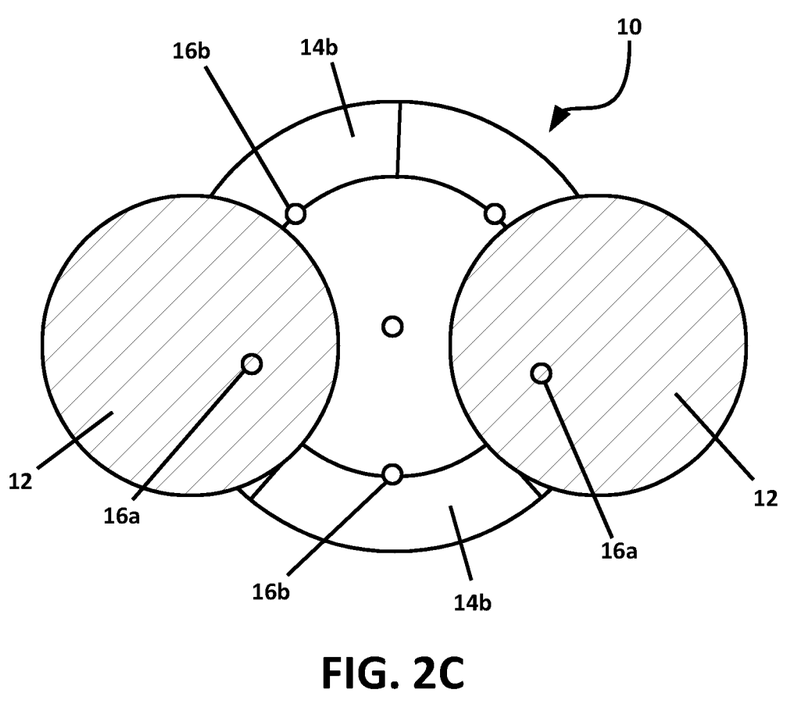
FIG. 2C shows a dual mask projected onto a lighthead having five (5) lighting partitions.

Furthermore, adjustment of light output is limited to the number of unique lighting partitions within the lighthead, wherein the light intensity of each lighting partition is independently controlled. A lighting system may have a lighthead with one (1) proximity sensor associated with each lighting partition to determine whether there is a blockage between the lighthead and the work area. As shown in FIG. 2A, a lighthead 10 can have six (6) partitions 14 with a respective number of sensors 16. Each partition has a plurality of associated LEDS. When one or more masks 12 span multiple lighting partitions 14 of the lighthead 10 (see FIGS. 2B and 2C), blocked sensors 16a correspond to the blocked lighting partitions of the lighthead 10. The light output from the unblocked sensors 16b corresponding to the unblocked partitions 14b is increased to compensate for the blockage. The blockage problem can be mitigated by increasing the number of unique lighting partitions of the lighthead. However, such an increase in the number of partitions results in a significant increase in engineering complexity, electrical inefficiency, lighthead size, and manufacturing cost.

In another aspect of the present invention, about 90% of surgical lighting installations in operating theaters include two lightheads. A small number (about 5-10%) of installations have three or more lightheads. Multiple lightheads are used in conjunction during an operation to provide supplemental lighting by focusing both beams to a single spot. This is known as "co-illumination" or "aggregation" and is intended to minimize shadowing effects on the work area by providing greater angular source distribution and to increase the amount of visible light.

The present invention provides a new and improved shadow control system and co-illumination detection system.

SUMMARY OF THE INVENTION

In accordance with the present invention, there is provided an adaptive shadow control system for a surgical lighting system.

In accordance with another aspect of the present invention, there is provided an adaptive shadow control system that includes enable/disable control logic.

In accordance with yet another aspect of the present invention, there is provided a control system for detecting co-illumination in a surgical lighting system in order to activate and/or deactivate an adaptive shadow control system.

In accordance with still another aspect of the present invention, there is provided a control system for a surgical lighting system in which non-partitioned lightheads can be implemented, reducing cost and complexity of the surgical lighting system.

In accordance with still another aspect of the present invention, there is provided a surgical lighting system comprising: a first lighthead for illuminating a work area, said first lighthead formed as a unitary lighthead assembly; a first sensor assembly associated with the first lighthead for detecting blockage of light between the first lighthead and the work area; a second lighthead for illuminating the work area, said second lighthead formed as a unitary lighthead assembly; and an adaptive shadow control for receiving a blockage detection signal from the first sensor assembly and increasing the light output from the unitary lighthead assembly of at least one of the lightheads to compensate for the blockage.

In accordance with still another aspect of the present invention, there is provided a surgical lighting system comprising: a plurality of lightheads for illuminating a work area, each of said lightheads having respective lighting modules that are pulsed between ON and OFF states, wherein the respective lighting modules of each lighthead are pulsed out of phase; a first sensor assembly associated with one of the lighthead to detect asynchronous ON and OFF pulsations from the lighting modules; a control system for determining whether the signals detected by the sensor assembly are within a threshold light level indicative of a co-illumination lighting mode resulting from an aggregated light pattern of overlapping light beams from a plurality of lightheads; and an adaptive shadow control function of the control system for adjusting light output produced by at least one of the lightheads, wherein said adaptive shadow control function is activated in response to the detected co-illumination lighting mode.

In accordance with still another aspect of the present invention, there is provided a process for controlling a surgical lighting system including a plurality of lightheads, the process comprising: detecting blockage of at least one of the plurality of lightheads between the lighthead and a work area; detecting a co-illumination lighting mode resulting from overlapping light beams from more than one of the plurality of lightheads into a single light pattern at a work area; and in response to detecting both the blockage and the co-illumination lighting mode, activating an adaptive shadow control for varying light output from at least one of the lightheads to the work area.

An advantage of the present invention is the provision of an adaptive shadow control system that compensates for blockage of a first lighthead using increased light output from a second lighthead.

Another advantage of the present invention is the provision of an adaptive shadow control system that provides improved shadow control.

Still another advantage of the present invention is the provision of an adaptive shadow control system that uses a full lighthead to compensate for loss of illumination due to blockage of another lighthead in the lighting system.

Still another advantage of the present invention is the provision of an adaptive shadow control system that allows lightheads to be configured with less excess light output capacity and to have less complexity (e.g., eliminating the need for individual control of lighting partitions within a single lighthead).

Yet another advantage of the present invention is the provision of an adaptive shadow control system that can be automatically enabled when it is detected that multiple lightheads are used in conjunction with each other in a "co-illumination" mode to aggregate respective light beams, thereby forming a single light pattern at a work area.

Yet another advantage of the present invention is the provision of an adaptive shadow control system that includes enable/disable control logic which uses asynchronous operation of each lighthead of a lighting system to determine whether the respective light beams of multiple lightheads are being aggregated for co-illumination at a single location in a work area.

A still further advantage of the present invention is the provision of an adaptive shadow control system that reduces surgical staff workloads and distractions caused by lighting adjustment, light intensity maintenance, and repositioning of lightheads.

These and other advantages will become apparent from the following description of illustrated embodiments taken together with the accompanying drawings and the appended claims.

BRIEF DESCRIPTION OF THE DRAWINGS

The invention may take physical form in certain parts and arrangement of parts, an embodiment of which will be described in detail in the specification and illustrated in the accompanying drawings which form a part hereof, and wherein.

DETAILED DESCRIPTION OF THE INVENTION

Figure 3:
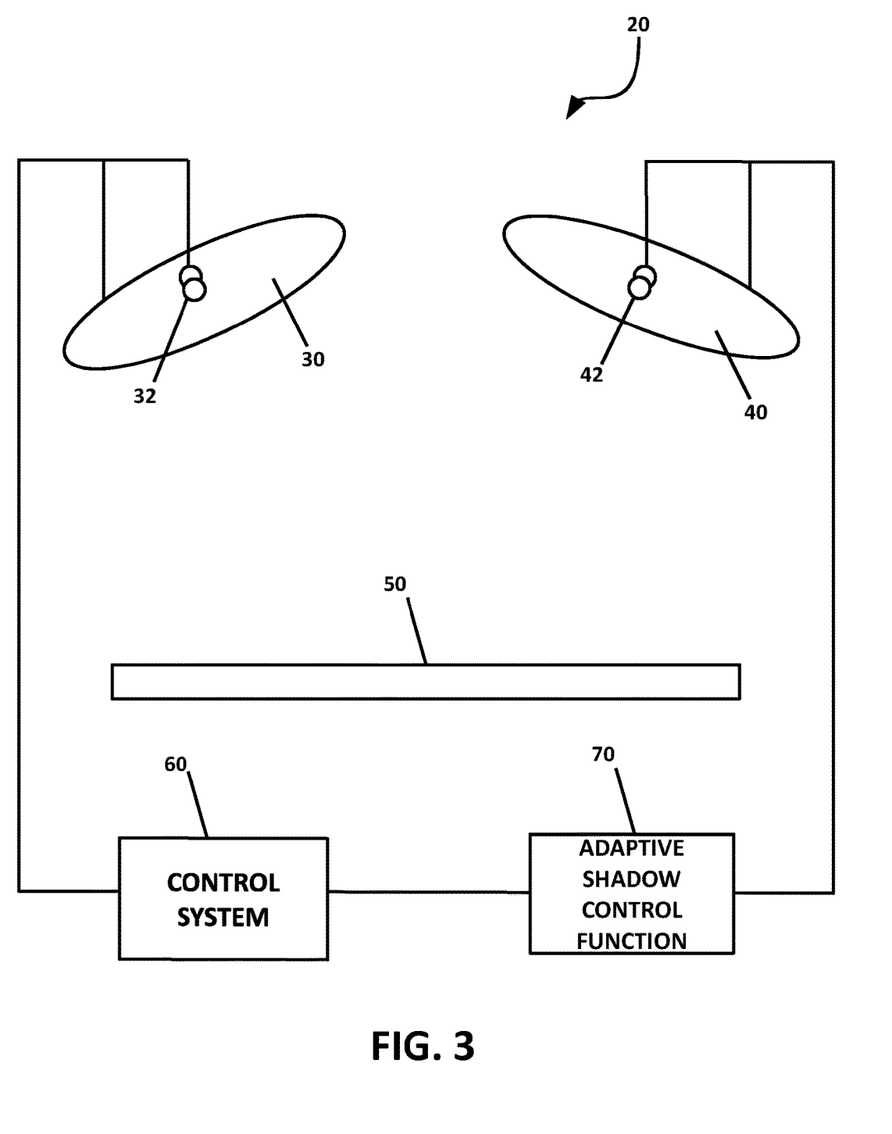
FIG. 3 depicts an exemplary control system used in conjunction with a pair of surgical lightheads.

Referring now to the drawings wherein the showings are for the purposes of illustrating an embodiment of the invention only and not for the purposes of limiting same, the present invention is directed to an adaptive shadow control system for a surgical lighting system. As shown in FIG. 3, a lighting system 20 is comprised of two lightheads 30, 40 where each lighthead 30, 40 includes at least one lighting module having one or more light elements, which can be LEDs. The lightheads 30, 40 illuminate a work area (e.g., a surgical site of a surgical patient supported by a surgical table 50). In accordance with an embodiment of the present invention, sensor assemblies 32, 42, are associated with each respective lighthead 30, 40 (e.g., mounted to the lighthead housing) to detect whether there is a blockage, between the lighthead and the work area, that is blocking at least a portion of the associated light beam emitted by one or both of the lightheads 30, 40. The sensor assemblies 32, 42 may detect blockage of light beams directly or indirectly. For example, the sensor assemblies 32, 42, may take the form of a proximity sensor or an image sensor to directly sense a blockage. Alternatively, the sensor assemblies 32, 42, may take the form of a light sensor that senses a loss of luminance to indirectly sense a blockage. It should be appreciated that the sensor assemblies 32, 42, may be alternatively located proximate to the work area rather than mounted to the respective lightheads 30, 40. Furthermore, it is contemplated that multiple sensors can be used in combination.

The lighting system 20 of FIG. 3 also includes a control system 60 that receives signals from the sensor assemblies 32, 42 and controls the light output from the lightheads 30, 40 using an adaptive shadow control function 70. For the purpose of illustrating an embodiment of the present invention, a lighting system with two (2) lightheads 30, 40 will be described herein. However, it should be understood that this is not intended to limit the scope of the present invention, since it is contemplated that the present invention may be implemented in connection with lighting systems that include more than two lightheads.

Figure 4A:
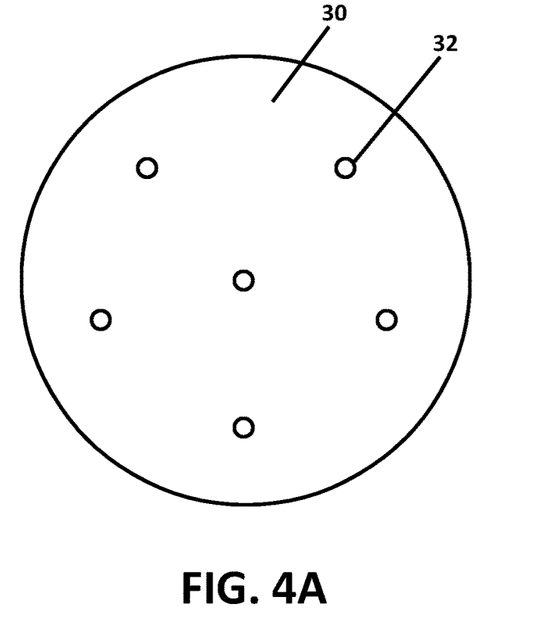
FIG. 4A shows a single lighthead having five (5) sensor assemblies.
Figure 4B:
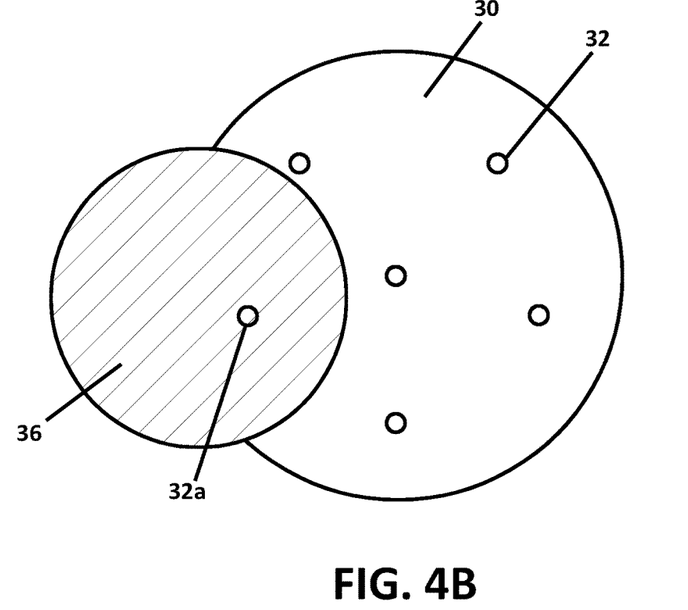
FIG. 4B shows a single mask projected onto a single lighthead having five (5) sensor assemblies.
Figure 4C:
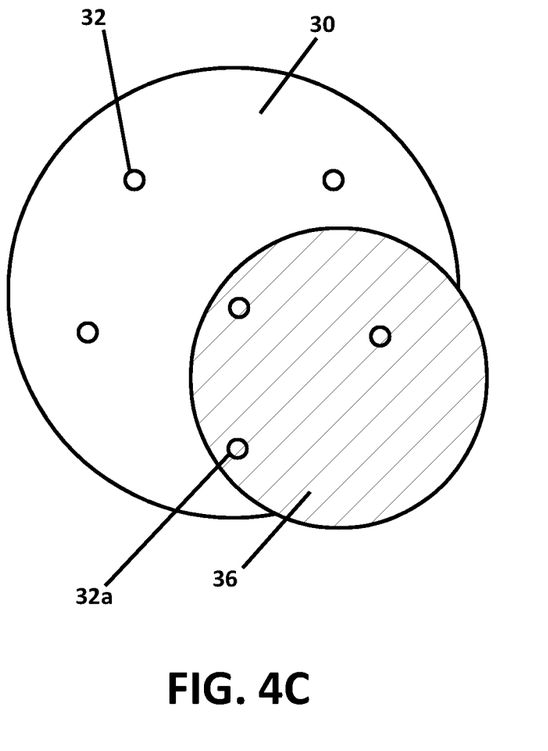
FIG. 4C shows a dual mask projected onto a lighthead having five (5) lighting sensor assemblies.

An exemplary lighthead 30 is shown in FIG. 4A. As depicted, the lighthead 30 includes a single lighting unit formed as a unitary lighthead assembly without individual lighting partitions, with a single control governing the operation of the entire lighthead. The lighthead 30 as shown includes six (6) sensor assemblies 32, arranged in a substantially pentagonal configuration. However, it is to be appreciated and understood that any desirable number of sensor assemblies 32 in any desirable configuration can be implemented without departing from the inventive concept disclosed herein. As shown in FIGS. 4B and 4C, these sensor assemblies 32 can detect the position of the blockage of the lighthead 30. If more than one sensor assembly 32a is blocked by one or more obstructions 36 (e.g., a surgeon's head), the system can estimate the degree of blockage of the lighthead 30. In a special aspect of the present invention, the lighthead 30 is a single assembly formed of respective lighting modules, and is not divided into lighting partitions as with previous-type lightheads.

If a blockage of a light beam associated with the first lighthead 30 is detected by the sensor assembly 32, then the control system 60 implements the adaptive shadow control function 70 of the present invention by compensating for this blockage with increased light output from the second lighthead 40. Conversely, if a blockage of a light beam associated with the second lighthead 40 is detected by the sensor assembly 42, then the control system 60 implements the adaptive shadow control function 70 of the present invention to compensate for this blockage with increased light output from the first lighthead 30.

By compensating for a loss of luminance at the surgical site from a blocked lighthead through increased light output from an unblocked lighthead, the excess lighting capacity required for total compensation is reduced to 50% per lighthead. Since individual lightheads can be freely positioned, it is assumed that one lighthead may be positioned such that it incurs little or no blockage.

Figure 5:
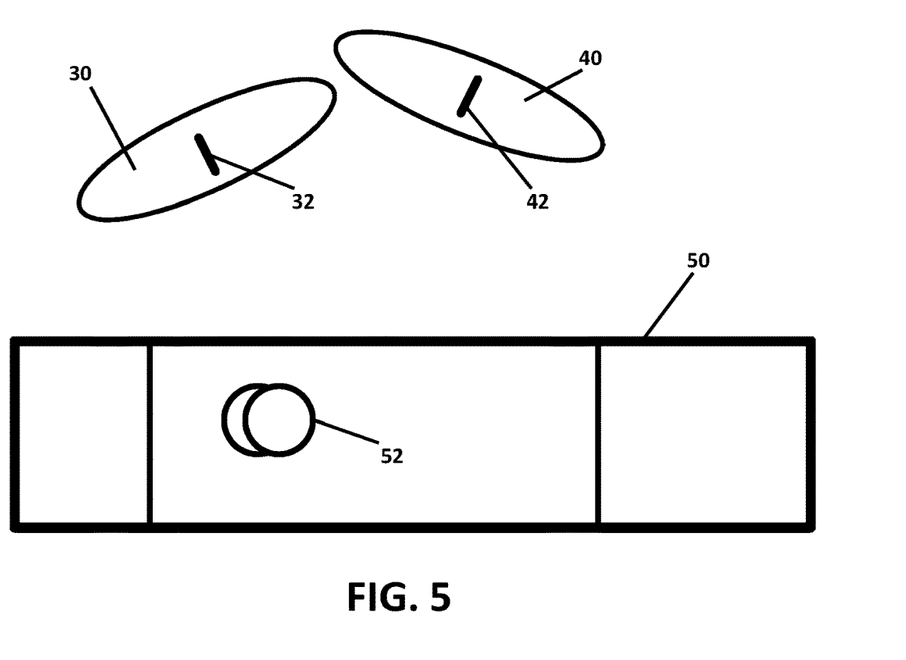
FIG. 5 shows a system having a pair of lightheads operating in a co-illumination lighting mode that produces overlapping, aggregated light patterns at a work area.

The adaptive shadow control function 70 is automatically enabled or disabled based on a detection of a mode of operation for the lightheads 30, 40. In a first mode of operation (i.e., a co-illumination lighting mode), the respective light beams produced by the two lightheads 30, 40 are positioned by a user to focus on a single work area at a single location, thereby producing an aggregated co-illumination light pattern 52 in which the light beams from each lighthead 30, 40 overlap (see FIG. 5). In the co-illumination lighting mode, the control system 60 enables the adaptive shadow control function 70. The control system 60 independently adjusts the light output produced by the two lightheads 30, 40 in order to dilute shadows in a desired operating area of the surgical patient in the surgical work area.

Figure 6:
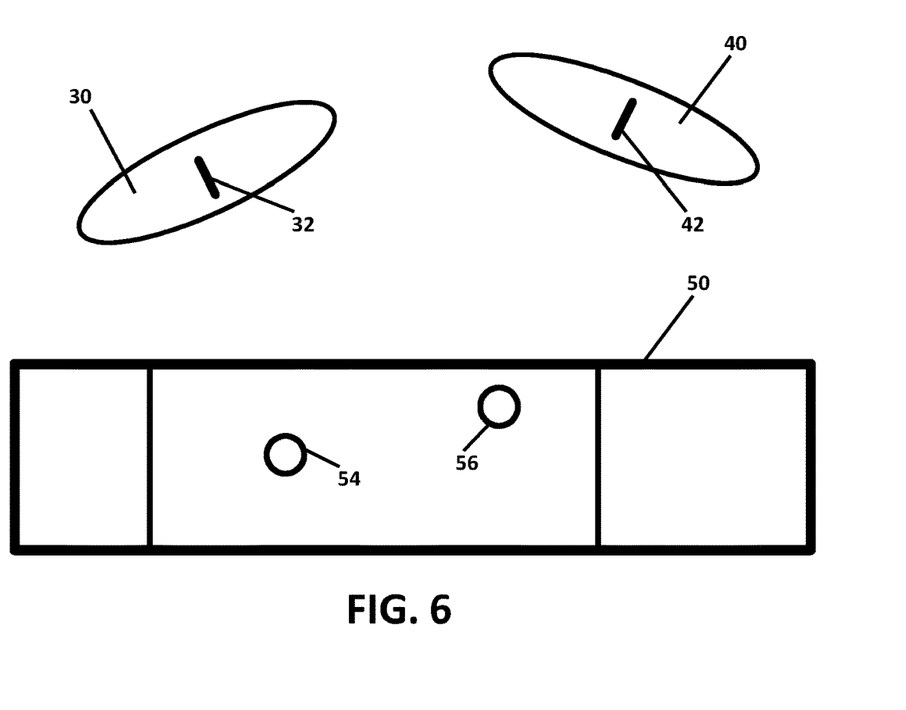
FIG. 6 shows a system having a pair of lightheads operating in an independent lighting mode that produces a pair of independent light patterns at different work areas.

In a second mode of operation (i.e., an independent lighting mode), the two lightheads 30, 40 are operated independently, such that the light beams emitted by the two lightheads 30, 40 are not overlapped (or "co-illuminating") at a single work area at a single location, thereby producing two (2) independent light patterns 54, 56 (see FIG. 6) at different work areas having respective different locations. If the control system 60 determines that the lighting system 20 is operating in an independent lighting mode, then the control system 60 disables the adaptive shadow control function 70 of the present invention.

In accordance with one embodiment of the present invention, the control system 60 automatically determines whether the lightheads 30, 40 are operating in (i) a co-illumination lighting mode or (ii) an independent lighting mode, by operating the lightheads 30, 40 asynchronously. In this regard, the lighting modules (i.e., LEDs) of the first and second lightheads 30, 40 are asynchronously pulsed ON and OFF such that the LEDs of the first lighthead 30 have an OFF period while LEDs of the second lighthead 40 have an ON period concomitantly (see waveforms A and B of FIG. 7). The lighting modules in each lighthead 30, 40 are pulsed very rapidly, so that the light pulsates at a frequency faster than can be visually detected by the human eye (which cannot observe pulsations faster than a frequency of 30 Hz). The selected pulse frequency should be too high for human eye detection, but at a frequency where the light pulses are detectable by a sensor. The light of both lightheads 30, 40 are pulsed 180 degrees out of phase with each other, giving the human eye the perception that the co-illumination is continuous and at constant intensity. This perceived continuous illumination intensity is represented by the illumination of both lightheads 30, 40 in the ON state averaged out over the span of a duty cycle.

It should be appreciated that while an embodiment of the present invention is described with pulsation of the lightheads 180 degrees out of phase with each other, the degrees of phase shift may be changed to accommodate a lighting system with more than two (2) lightheads.

Figure 7:
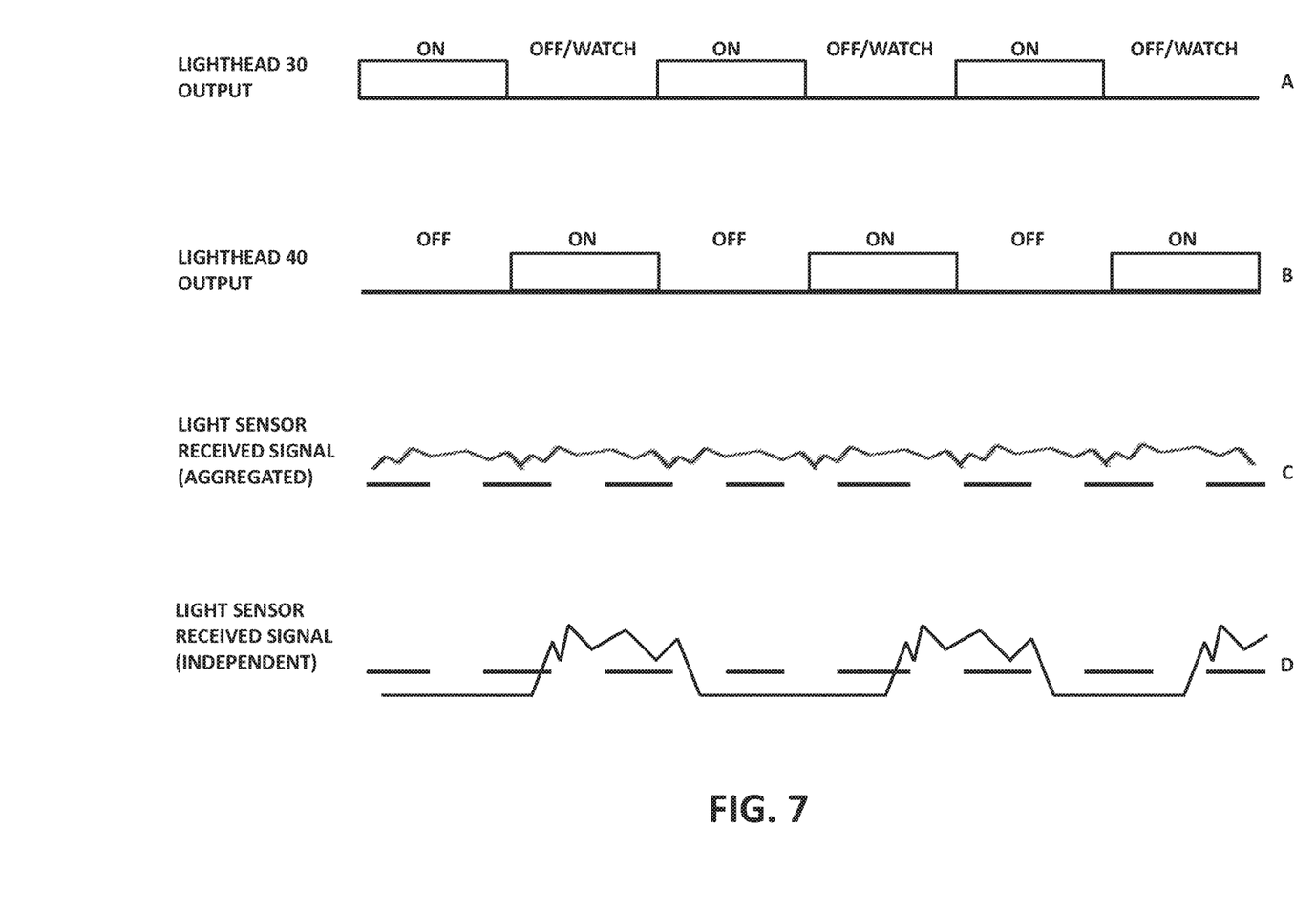
FIG. 7 illustrates the signals for detecting whether a lighthead is operating in a co-illumination or independent lighting mode, according to an embodiment of the present invention.

The sensor assembly 32 of the first lighthead 30 includes a light sensor (e.g., photodiodes or phototransitors mounted to the lighthead housing) that senses the amount of incident light during the OFF period for the first lighthead 30 (see waveforms C and D of FIG. 7). The light sensor detects the total light reflecting from the illuminated area and generates signals corresponding to the detected illumination level. These signals are transmitted to the control system 60, which uses the signals to control the operation of the lightheads 30, 40.

If the amount of incident light sensed by the light sensor during the OFF period of the first lighthead exceeds a predetermined threshold light level (indicated by the dashed line in waveform C), then the control system 60 determines that the first and second lightheads 30, 40 are operating in a co-illumination lighting mode (i.e., pointing their respective light beams at a single work area at a single location to form an aggregated co-illumination light pattern). In this instance, the control system 60 activates the adaptive shadow control function 70. Conversely, if the amount of incident light sensed by the light sensor during the OFF period of the first lighthead 30 does not exceed a predetermined threshold light level (indicated by the dashed line in waveform D), then the control system 60 determines that the first and second lightheads 30, 40 are operating in the independent lighting mode (i.e., pointing their respective light beams at two different work areas in respectively different locations).

As depicted in FIG. 7, in order to detect the operating mode of the lightheads 30, 40, the control system 60 operates the lightheads 30, 40 asynchronously, 180 degrees out of phase with other, with the pulsed LEDs within the light modules of the first lighthead 30 having an OFF period at the same time that the light modules of second lighthead 40 have an ON period concomitantly. While the first lighthead 30 is in the OFF state, the sensor assembly 32 "watches" to detect the amount of light incident on the illuminated area. If the amount of detected incident light is determined to exceed the indicated threshold, it can be inferred that the two lightheads 30, 40 are pointing to a single spot, indicating a co-illumination operating mode. Essentially, the threshold (shown in waveforms C and D) indicates whether the sensor assembly 32 of the first lighthead 30 detects whether the light from the second lighthead 40 is shining in the same location, and thereby indicating co-illumination.

Determining whether lightheads are operated together in a co-illumination mode (i.e. pointed to a single spot) or operated separately in an independent mode can be accomplished automatically by employing a suitable technique. The adaptive shadow control function 70 of the control system 60 can preferably be operated on the following basis: 1) two lights are co-illuminating a single work area, and is detected and determined by the lightheads; 2) blockage of a lighthead is sensed; and 3) the loss of illumination is compensated by the secondary, or complementary, lighthead when both above conditions are met.

It should be noted that the first and second sensor assemblies 32, 42 can include both types of sensor elements described hereinabove to be used for determining both blockage and co-illumination. In one aspect, the sensor assemblies 32, 42 of one of the respective lightheads 30, 40 can be used to detect blockage while the sensor assemblies 32, 42 of the respective other of the lightheads 30, 40 can be used to detect co-illumination. Alternatively, in a multisensor configuration such as the pentagonal arrangement shown in the exemplary lighthead 30 of FIGS. 4A, 4B, and 4C, the blocked sensor assemblies 32a can be used to detect blockage while the unblocked sensor assemblies 32 of the same lighthead 30 can be used to detect co-illumination. Any combination of sensors from either of the sensor assemblies 32, 42 from either lighthead 30, 40 can be used to make the necessary determinations, all without departing from the invention.

The control system 60 preferably employs an automatic shadow control enabling algorithm that detects the blockage on a lighthead. The control system 60 also preferably employs detecting whether the light beams from each lighthead 30, 40 are aggregated into a single overlapping light pattern of aggregated, co-illuminated light. Such an algorithm 80 for "enabling" and "disabling" adaptive shadow control will now be described in connection with FIG. 8. In accordance with one embodiment of this algorithm, the respective sensor assemblies 32, 42 of each lighthead 30, 40 are used to detect whether there is a lighthead blockage or whether the lightheads 30, 40 are operating in the co-illumination lighting mode. If both a lighthead blockage and a co-illumination lighting mode are detected, then the adaptive shadow control function 70 is enabled. In contrast, if either the lighthead blockage or the co-illumination lighting mode is not detected, then the adaptive shadow control function 70 is disabled.

Figure 8:
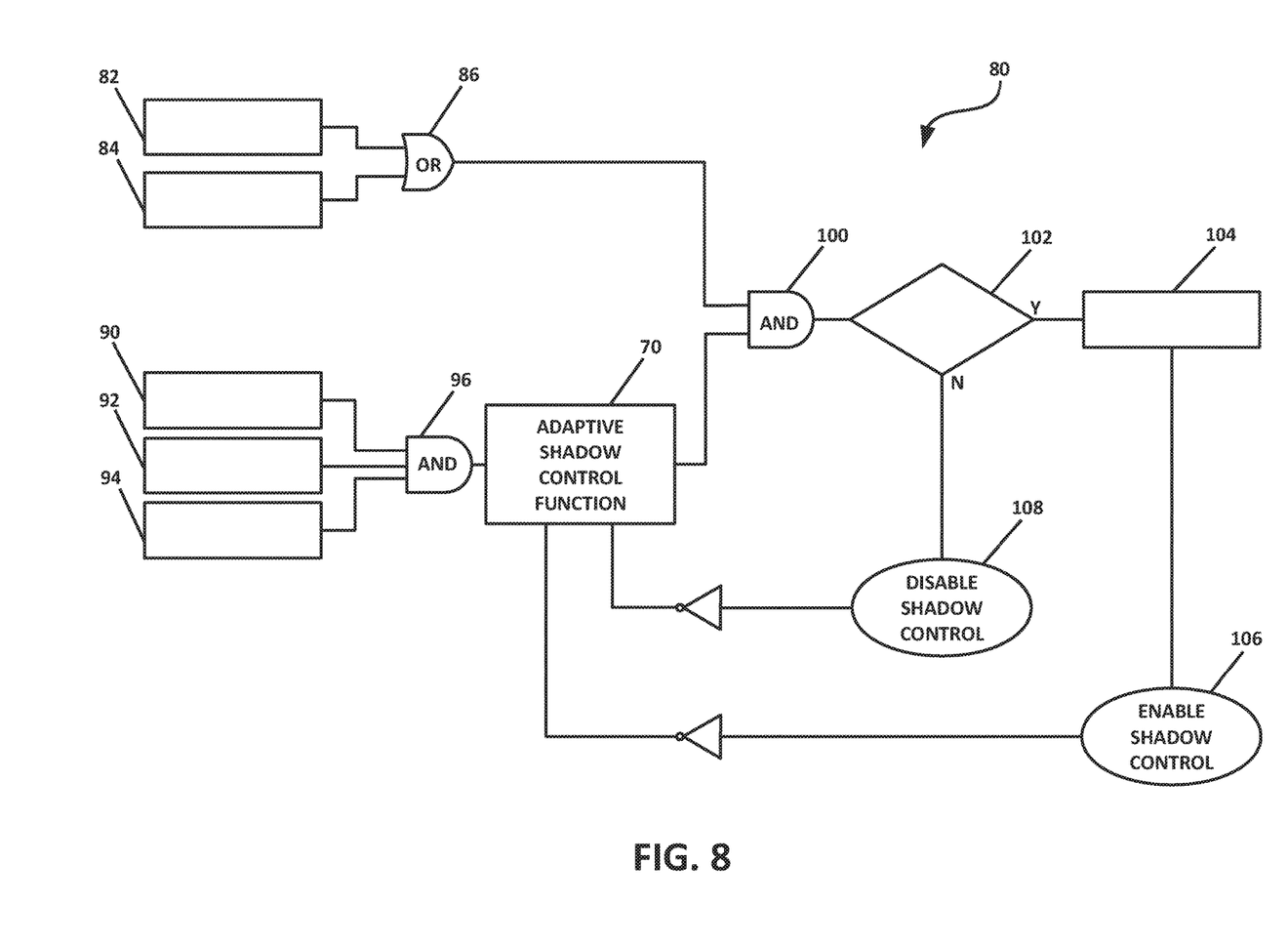
FIG. 8 illustrates control logic for enabling/disabling adaptive shadow control, according to an embodiment of the present invention.

The algorithm 80 as disclosed herein and depicted in FIG. 8 can be expressed in terms of Boolean logic gates (e.g., AND gates and OR gates) wherein system inputs and outputs are processed according to Boolean operations. Of course, it is to be understood that such an expression is not limiting and that other operational logic schemes can be employed without departing from the invention.

As specifically shown in the algorithm 80 of FIG. 8, either a first lighthead blockage 82 or a second lighthead blockage 84 can be detected by the sensor assemblies 32, 42 of the respective lightheads 30, 40. These blockage detections 82, 84 are received as "high" inputs and passed through an OR gate 86, such that if blockages 82, 84 are detected at either lighthead 30, 40, the OR gate 86 indicates a "high" output. If no blockage is detected at either lighthead 30, 40, the OR gate 86 indicates a "low" output.

As also shown in FIG. 8, a first lighthead co-illumination state 90 and a second lighthead co-illumination state 92 can be detected by the sensor assemblies 32, 42 of the respective lightheads 30, 40. These co-illumination detections 90, 92 along with an auto-enable command 94 are received as "high" inputs and passed through a first AND gate 96. If co-illumination states 90, 92 from both lightheads 30, 40 and also the auto-enable command 94 are received, the output of the first AND gate 96 is "high," and activates the adaptive shadow control function 70 of the control system 60. But if co-illumination states 90, 92 from either or both of the lightheads 30, 40 and also the auto-enable command 94 are not received, the output of the first AND gate 96 is "low," and a negative activation state is indicated (e.g., deactivation) of the adaptive shadow control function 70 of the control system 60. In other words, unless co-illumination states 90, 92 from both lightheads 30, 40 are indicated, additionally in combination with the auto-enable command 94, the adaptive shadow control 70 is not activated.

The outputs of the OR gate 86 and the adaptive shadow control function 70 are received as inputs at a second AND gate 100. If both of the inputs are "high," indicating blockage 82, 84 at least one of the lightheads 30, 40 and activation of the adaptive shadow control function 70, the output of the second AND gate 100 is "high." If one or both of the inputs are "low," indicating either no blockage at one or both lightheads 30, 40 or deactivation of the adaptive shadow control function 70, the output of the second AND gate 100 is "low." The output of the second AND gate 100 is processed at a decision block 102. A "high" output from the second AND gate 100 renders a "yes" (Y) result at the decision block 102 and activates compensation 104 which sends an "enable shadow control" signal 106 to the adaptive shadow control function 70, thereby maintaining activation. A "low" output from the second AND gate 100 renders a "no" result at the decision block 102 and sends a "disable shadow control" signal 108 to the adaptive shadow control function 70, thereby ensuring deactivation.

A control law for the control system 60 has three inputs, beside the auto enable function at the system level: 1) lightheadSensors, in which an integer number of sensors are used for detecting blockage in the lighthead under operation; 2) complementaryLightheadSensors, in which an integer number of sensors are used for detecting blockage from a second lighthead; and 3) co-illuminate, in which a "high" Boolean logic output from the lightheads 30, 40 corresponds to a determination that there are two spots co-illuminating a single work area.

Complementary lighthead compensation accuracy depends on the number of blockage detectors. With too few sensor assemblies 32 per lighthead 30, a surgeon's head partially blocking the lighthead 30 may not be detected, and no compensation can be applied. The error associated with the compensation is driven by the resolution of blockage detection. FIGS. 4A, 4B, and 4C show an embodiment in which six sensor assemblies 32 are implemented for a single lighthead 30 having a unitary assembly, without individual lighting modules, in a generally pentagonal arrangement around a central sensor assembly. A comparison follows of expected compensation and adaptive shadow control error for up to six sensor assemblies 32:

| No. of Heads, Sensors | Compensation | Typical Error |
|---|---|---|
| Single lighthead, no sensors | 0% | −15% |
| Dual lighthead, no sensors | | |
| Single lighthead, one sensor | 23% | +10%-15% |
| Dual lighthead, one sensor | | |
| Single lighthead, two sensors | 35% | +15%-15% |
| Dual lighthead, two sensors | | |
| Single lighthead, three sensors | 45% | +15%-15% |
| Dual lighthead, three sensors | | |
| More than three sensors | 55% | +15%-15% |

In addition to the benefits of the present system in providing adaptive shadow control, the present co-illumination detection system can be used for processing any number of automatic responses, including regulation of energy or adaptive shadow control of one or both of the lightheads 30, 40, changing intensity of one or both of the lightheads 30, 40, changing spectral distribution of one or both of the lightheads 30, 40, changing beam size of one or both of the lightheads 30, 40, adjusting aim of one or both of the lightheads 30, 40, or providing audible or visible indication that co-illumination has been detected, etc. Additionally, co-illumination detection can also be used to automatically regulate the maximum light intensity, to not exceed the limit of hazardous levels energy known to cause burning or dehydration of exposed tissue of the surgical patient. The limitation of the maximum light intensity is accomplished automatically by fading down at an imperceptible rate to the appropriate lighting condition. For example, if two surgical lightheads 30, 40 each at 160,000 lx (160 klx) were brought together to co-illuminate the surgical wound, the control system 60 could detect the co-illumination and fade down to 100,000 lx each over a period of time. The additive light would result in 200,000 lx instead of the more hazardous level of 320,000 lx. Another implementation may be to govern each intensity setting by a scaling factor, rather than having a single maximum value.

Other approaches contemplated for determining whether multiple lightheads 30, 40 are being used together to co-illuminate light beams at a single location (i.e., used in an aggregated co-illumination lighting mode), include, but are not limited to: asynchronous lighthead LED pulse operation (pulse-watch through photodiodes); positional encoders located in arms or joints of the suspension system supporting the lightheads 30, 40 for determining the position and pointing direction of the lightheads 30, 40; proximity detectors (e.g., Hall Effect, field strength, and ultrasonic) for sensing the locality of the edge of each of the lighthead 30, 40; a secondary sensor and transmitter (infrared, for example); a triangulation network (similar to GPS) for determining lighthead 3-D coordinates, and supplementing sensors in the lightheads 30, 40 for determining lighthead aim (such as inclinometers); and boresight aiming (laser scattering), which is similar to the asynchronous light operation, where lasers are deployed by each of the lightheads 30, 40 that uniquely identifies each lighthead (e.g., by color or asynchronous operation).

The present invention provides a novel active shadow control system implemented to use a full lighthead without requiring individual lighting partitions to compensate for a blocked lighthead. The present system also provides improved shadow control and intensity maintenance compared to a prior art passive lighting system due to the detection of blockage and individual adjustment of intensity between the plurality of lightheads without requiring individual lighting partitions. The present system also provides improved workload and reduces distraction of surgical staff due to automatic adjustment. Repositioning of lightheads by the surgical staff is also minimized.

The present invention also provides utilization of a full lighthead without requiring a lighthead having individual lighting partitions within the surgical lighting system to compensate for loss of illumination due to blockage. Full lighthead compensation requires less excess capacity, and less complexity within a single lighthead since individual control of lighting partitions is no longer required. By eliminating the necessity of individual lighting partitions, the present system reduces engineering complexity, electrical inefficiency, and lighthead size associated with the system and thereby reduces the expense associated with manufacture and maintenance of the lightheads.

The foregoing describes specific embodiments of the present invention. It should be appreciated that these embodiments are described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A surgical lighting system comprising:
   a first lighthead for emitting a light beam to illuminate a work area, said first lighthead formed as a unitary lighthead assembly, wherein said first lighthead includes at least one lighting module having one or more light elements;
   a second lighthead for emitting a light beam to illuminate the work area, said second lighthead formed as a unitary lighthead assembly, wherein said second lighthead includes at least one lighting module having one or more light elements;
   a first sensor for detecting a blockage of the light beam emitted by the first lighthead;
   an adaptive shadow control for receiving a signal from the first sensor indicative of detecting the blockage of the light beam emitted by the first lighthead and increasing light output from the second lighthead to compensate for the blockage of the light beam emitted by the first lighthead; and
   a control system configured for detecting a signal indicative of (i) a co-illumination lighting mode resulting from overlapping of the light beams emitted from the first and second lightheads to form a single aggregated light pattern on the work area, or (ii) an independent lighting mode resulting from independent operation of the first and second lightheads such that the light beams emitted from the first and second lightheads do not overlap to form a single aggregated light pattern on the work area.

2. A surgical lighting system according to claim 1, wherein the first sensor is a light sensor for sensing a loss of luminance to indirectly detect the blockage of the light beam emitted by the first lighthead.

3. A surgical lighting system according to claim 1, wherein the first sensor is a proximity sensor or an image sensor to directly detect the blockage of the light beam emitted by the first lighthead.

4. A surgical lighting system according to claim 1, wherein the surgical lighting system includes a plurality of sensors for detection of a blockage of the light beam emitted by the first lighthead, wherein detection of the blockage of said light beam by more than one of the sensors corresponds to an estimated degree of blockage of the light beam emitted by the first lighthead.

5. A surgical lighting system according to claim 1, wherein the control system is configured to disable operation of the adaptive shadow control upon detecting the signal indicative of the independent lighting mode.

6. A surgical lighting system according to claim 1 wherein the surgical lighting system includes a light sensor for sensing a level of reflected light from the work area, said light sensor generating a signal corresponding to a sensed illumination level.

7. A surgical lighting system according to claim 1, further comprising a second sensor associated with the second lighthead for detecting a blockage of the light beam emitted by the second lighthead to illuminate the work area, wherein the adaptive shadow control receives a signal from the second sensor indicative of detecting the blockage of the light beam emitted by the second lighthead and increases light output from the first lighthead to compensate for the blockage of the light beam emitted by the second lighthead.

8. A surgical lighting system comprising:
a plurality of lightheads for respectively emitting a light beam to illuminate a work area, each of said lightheads having respective lighting modules that are asynchronously pulsed between ON and OFF states, wherein the respective lighting modules of each lighthead are asynchronously pulsed such that lighting modules of only one of the lightheads are ON while the lighting modules of the other lightheads are OFF;
a first sensor for detecting the asynchronous pulsations of the ON and OFF states of the lighting modules;
a control system configured for detecting a signal indicative of (i) a co-illumination lighting mode resulting from overlapping of the light beams emitted from the plurality of lightheads to form a single aggregated light pattern on the work area, or (ii) an independent lighting mode resulting from independent operation of the plurality of lightheads such that the light beams emitted from the plurality of lightheads do not overlap to form a single aggregated light pattern on the work area; and
an adaptive shadow control function for adjusting light output from at least one of the plurality of lightheads in response to blockage of at least one of the light beams, wherein said control system enables the adaptive shadow control function in response to detection of the co-illumination lighting mode and disables the adaptive shadow control function in response to detection of the independent lighting mode.

9. A surgical lighting system according to claim 8, wherein the lighting modules of the plurality of lightheads are asynchronously pulsed between the ON and OFF states at a predetermined pulsation frequency that cannot be visually detected.

10. A surgical lighting system according to claim 8, further comprising a second sensor for detecting a blockage of one of the light beams emitted by one of the plurality of lightheads, wherein the adaptive shadow control function varies operation of at least one of the lightheads such that the light output produced by at least one of the plurality of lightheads is increased in response to the blockage detected by the second sensor.

11. A process for controlling a surgical lighting system including a plurality of lightheads, the process comprising:
detecting a signal indicative of whether there is a blockage of a light beam emitted by at least one of the plurality of lightheads to illuminate a work area;
detecting a signal from a sensor that indicates (i) a co-illumination lighting mode resulting from overlapping of the light beams emitted from a plurality of lightheads to form a single aggregated light pattern on the work area, or (ii) an independent lighting mode resulting from independent operation of the plurality of lightheads such that the light beams emitted from the plurality lightheads do not overlap to form a single aggregated light pattern on the work area; and
enabling operation of an adaptive shadow control when the co-illumination lighting mode is detected and disabling the adaptive shadow control when the independent lighting mode is detected, said adaptive shadow control varying light output from at least one of the plurality of lightheads in response to detecting said blockage.

12. A process according to claim 11, further comprising said adaptive shadow control increasing the light output from at least one of the plurality of lightheads to provide additional illumination to the work area in response to detecting said blockage.

13. A process according to claim 11, wherein the process includes asynchronously pulsing the plurality of lightheads between an ON state and an OFF state.

14. A process according to claim 11, wherein each of the plurality of lightheads is pulsed out of phase between and an ON state and an OFF state.

* * * * *